(12) United States Patent
Schwartz et al.

(10) Patent No.: US 6,630,444 B1
(45) Date of Patent: Oct. 7, 2003

(54) INTESTINAL FUNCTION USING LEPTIN

(75) Inventors: Marshall Schwartz, Bryn Mawr, PA (US); Darlise O'Connor, Newark, DE (US)

(73) Assignee: The Nemours Foundation, Wilmington, DE (US)

( * ) Notice: Subject to any disclaimer, the term of this patent is extended or adjusted under 35 U.S.C. 154(b) by 0 days.

(21) Appl. No.: 09/693,864

(22) Filed: Oct. 23, 2000

(51) Int. Cl.[7] ............ A61K 38/00; C07K 2/00; C07K 14/00
(52) U.S. Cl. ............ 514/2; 514/12; 424/184.1; 424/198.1; 424/85.1; 530/350; 530/399
(58) Field of Search ............ 424/85.1, 184.1, 424/198.1; 514/2, 12; 530/300, 350, 351, 399

(56) References Cited

PUBLICATIONS

Ulshen et al. Luminal epidermal growth factor preserves mucosal mass of small bowel in fasting rats. Clin Sci 90: 427–431, 1996.*

Alavi et al. Leptin: a new growth factor for the small intestine. J Pediatric Surg 37(3): 327–330, 2002.*

Hill et al. Leptin: its pharmacokinetics and tissue distribution. Int J Obesity 22: 765–770, 1998.*

Ceddia et al. Leptin increases glucose transport and utilization in skeletal muscle in vitro. Gen Pharmac 31(5): 799–801, 1998.*

Fruhbeck et al. Relation between leptin and the regulation of glucose metabolism. Diabetlologia 43: 3–12, 2000.*

Lostao et al. Presence of leptin receptors in rat small intestine and leptin effect on sugar absorption. FEBS Letters 423: 302–306, 1998.*

Maffei et al. Leptin levels in human and rodent: measurement of plasma leptin and ob RNA in obese and weight–reduced subjects. Nat Med 1(11): 1155–1161, 1995.*

Molina et al. Serum leptin concentrations in patients with short–bowel syndrome. Clin Nutrit 19(5): 333–338, 2000.*

Morton et al. Leptin action in intestinal cells. J Biol Chem 273(40): 26194–26201, 1998.*

Pearson et al. Novel effect of leptin on small intestinal absorptive capacity after massive small bowel resection. J Surgical Res 93(2): P54, 2000.*

Raguso et al. Leptin and the gastrointestinal tract. Curr Opin gastroenterol 16(2): 160–165, 2000.*

Gal et al. Characterization and localization of leptin receptors in the rat kidney. FEBS Letters 404:185–191, 1997.*

* cited by examiner

Primary Examiner—Elizabeth Kemmerer
Assistant Examiner—Bridget E. Bunner
(74) Attorney, Agent, or Firm—McGuireWoods LLP (57) ABSTRACT

A method for treating a patient that has inadequate intestinal function is described. Administering leptin to a subject increases the intestinal function beyond that for a normal intestine and beyond that of a normal adaptive response. Further, administering leptin to a subject results in an increase in amino acid absorption, sugar absorption, mucosal mass, transport mechanisms for amino acids, or transport mechanisms for sugars. The method may be used for treating subjects have conditions such as short bowel syndrome, inflammation of the bowel, necrotizing enterocolitis, intestinal atresia, midgut volvulus, severe acute gastroenteritis, chronic gastroenteritis, cholera, chronic infections of the bowel, immunologic disorders affecting the small intestine, and inflammatory bowel disease such as, chronic ulcerative colitis and Crohn's Disease.

9 Claims, 5 Drawing Sheets

SEQUENCE LISTING

```
<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 1
ggtcggtgtg aaccggatt                                                  19

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 2
gagatgatga ccctttg                                                    18

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 3
ggacttcgag gcctgatgct gtc                                             23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 4
gtaactggtg atggactgga tgt                                             23

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Primer
```

-continued

```
<400> SEQUENCE: 5
ggtacaacgt ggctgctgtc aac                                              23

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 6
cctgcacata ttccaaccag aagt                                             24
```

INTESTINAL FUNCTION USING LEPTIN

FIELD OF THE INVENTION

The present invention relates broadly to enhancing the functions of the small intestine and the treatment of inflammatory bowel diseases in a patient by the administration of leptin.

BACKGROUND OF THE INVENTION

Short bowel syndrome ("SBS") is a devastating clinical disorder resulting from massive small bowel resection. SBS affects many infants and children and threatens normal growth and development. The remnant intestine naturally adapts to resection, however, this adaptation process is often inadequate to meet the patients fluid and nutritional goals. There is no effective treatment and current management includes total parenteral nutrition ("TPN"), which itself is a source of significant morbidity and mortality. Accordingly, there is a need for an alternative method of management for short bowel syndrome. Other disorders of the small intestine can render the bowel nonfunctional for a prolonged period of time such as severe infection and inflammatory bowel disease.

SUMMARY OF THE INVENTION

It is an object of the present invention to provide an alternative method for management for short bowel syndrome and other disorders of the intestine.

Accordingly, the present invention includes a method for treating a patient comprising the step of administering leptin to a subject having a condition resulting from inadequate intestinal function. Leptin may be administered in an amount ranging from about 1 µg/kg body weight/day to about 50 µg/kg body weight/day. In another embodiment leptin may be administered in an amount ranging from about 2 µg/kg body weight/day to about 20 µg/kg body weight/day. The patient may have a condition selected from the group consisting of short bowel syndrome, inflammation of the bowel, inflammatory bowel disease (such as, chronic ulcerative colitis and Crohn's Disease), necrotizing enterocolitis, intestinal atresia, midgut volvulus, severe acute gastroenteritis, chronic gastroenteritis, cholera, chronic infections of the bowel, and immunologic disorders affecting the small intestine.

In accordance with one embodiment of the present invention leptin may be administered systemically. In another embodiment leptin may be administered luminally.

Further, leptin may be administered with nutritional supplements or with growth factors that increase the function of the intestine. In a preferred embodiment, the growth factors may be selected from the group consisting of HGF, EGF, IGF-1, IL-11, and GLP-2.

The present invention includes a method for supplying nutrients to a subject comprising the steps of providing nutrients to the subject and administering leptin to the subject in an amount effective to increase the absorption of the nutrients in the intestine of the subject. Leptin may be administered in an amount ranging from about 1 µg/kg body weight/day to about 50 µg/kg body weight/day. In another embodiment, leptin may be administered in an amount ranging from about 2 µg/kg body weight/day to about 20 µg/kg body weight/day. The subject may have a condition selected from the group consisting of short bowel syndrome, inflammation of the bowel, inflammatory bowel disease (such as, chronic ulcerative colitis and Crohn's Disease), necrotizing enterocolitis, intestinal atresia, midgut volvulus, severe acute gastroenteritis, chronic gastroenteritis, cholera, chronic infections of the bowel, and immunologic disorders affecting the small intestine. Leptin may be administered systemically or luminally.

Still further, the present invention includes a method for treating the intestine in a subject comprising the step of administering leptin to the subject in an amount effective to increase the intestinal function of the intestine. Still further, the method includes an amount of leptin that is effective to increase sugar absorption. The method may include an amount of leptin that is effective to increase amino acid absorption. Further, the method may include an amount of leptin that is effective to increase mucosal mass of the intestine. The amount of leptin ranges from 1 µg/kg body weight/day to about 50 µg/kg body weight/day. In another embodiment, leptin may be administered in an amount ranging from about 2 µg/kg body weight/day to about 20 µg/kg body weight/day. The subject may have a condition selected from the group consisting of short bowel syndrome, inflammation of the bowel, inflammatory bowel disease (such as, chronic ulcerative colitis and Crohn's Disease), necrotizing enterocolitis, intestinal atresia, midgut volvulus, severe acute gastroenteritis, chronic gastroenteritis, cholera, chronic infections of the bowel, and immunologic disorders affecting the small intestine. The leptin may be administered systemically or luminally.

Leptin may be administered with nutritional supplements or with growth factors that increase the function of the intestine. In a preferred embodiment, the growth factors may be selected from the group consisting of HGF, EGF, IGF-1, IL-11, and GLP-2.

The method also includes increasing intestinal function beyond the function of the normal intestine. The method also includes increasing intestinal function beyond the normal adaptive response.

DETAILED DESCRIPTION OF PREFERRED EMBODIMENTS

Leptin, a 167 amino acid (16 kD) cytokine, is a peptide product of the obesity (ob) gene and is expressed in a wide variety of tissues, including adipocytes, the human placenta, the gastric epithelium, and the mammary gland. Leptin regulates appetite and metabolic activity in mice by acting through the long form of the leptin receptor (OB-Rb) in the hypothalamus. Recently, leptin has been demonstrated to have angiogenic activity in vivo and in vitro. The receptor for leptin is a single transmembrane protein most closely related to the gp 130 signal-transduction component of class I cytokine receptors, such as IL-6, IL-11, G-CSF and LIF.

It has been discovered that administering leptin to a patient results in an increase in intestinal function when compared to the function of the normal intestine. Intestinal function as used herein, means amino acid absorption, sugar absorption, mucosal mass, transport mechanisms for amino acids, or transport mechanisms for sugars. Specifically, it has been found that the administration of leptin to a subject increases amino acid absorption, increases sugar absorption, increases in mucosal mass, and increases the transport mechanisms for the transportation of amino acids and sugars into the mucosa of the small intestine.

After massive small bowel resection, the remaining intestine spontaneously undergoes an adaptive response in which the bowel wall thickens and the absorptive surface of the villi increases. The adaptive response increases the absorptive capacity of the mucosa per unit area. Despite this naturally occurring phenomenon, the adaptation frequently is not enough to maintain adequate absorption of nutrients needed to sustain growth. When the adaptive response is insufficient to meet the nutritional needs of the patient, short bowel syndrome ("SBS")is the result. This is particularly devastating to children, who have increased caloric requirements in order to support normal growth and development. There is a high mortality rate in the pediatric age group from complications such as liver failure, sepsis, and malnutrition. Treatments for SBS are parentally administered nutrients ("TPN"), surgically elongating the bowel, and small bowel transplantation which is usually accompanied by a liver transplant all of which have serious complications.

Importantly, it has been discovered that leptin not only increases the intestinal function of the intestine when compared to the function of the normal intestine, but also increases intestinal function beyond the normal adaptive response of the small bowel. Administering leptin to a subject increases the response of the small intestine epithelium during intestinal adaptation induced by massive bowel resection. Specifically, the administration of leptin increases carbohydrate absorption beyond the normal adaptive response.

Leptin may be administered in recombinant form or from natural sources. Leptin may be administered to patients at effective doses and for effective periods of time by the intestinal intralumenal route either by catheter or sustained release preparations or by systemic routes, including but not limited to intravenous administration. Suitable carriers for leptin may be found in Remington's Pharmaceutical Sciences, $18^{th}$ ed., 1990, Mack Publishing Co., Easton, Pa. Further, leptin may be administered intravenously, intramuscularly, intraperitoneal, and through other parenteral routes.

As used herein, an "effective dose" of leptin is that amount of leptin administered to a subject sufficient to increase intestinal function of the intestine of the subject. An effective dose of leptin ranges from about 1 µg/kg body weight/day to about 50 µg/kg body weight/day. Preferably, the effective dose of leptin ranges from about 2 µg/kg body weight/day to about 20 µg/kg body weight/day. The number of days leptin may be administered to the subject may vary depending on the condition. However, leptin should be administered for a long enough period to increase the intestinal function of the intestine. Leptin doses should be provided at intervals sufficient to maintain the increase in intestinal function of the intestine. The length of administration and the intervals may vary depending on the age, size and condition of the subject. Subjects or patients include, but are not limited to, mammals, rats, infants, children, adults, and seniors.

It will be appreciated that nutritional supplements, medications, and growth factors may be administered with an effective dose of leptin. Nutritional supplements or nutrients may include enteral formulas and glutamine. The nutritional supplements may be administered along with the leptin or alternatively the nutritional supplements may be provided separately by the same or different administration routes. For example, the administration of leptin may occur intravenously while the nutritional supplements are taken orally. Medications may include antibiotics, anti-diarrheal and inti-inflammatory drugs and may be provided with the leptin or administered separately. Growth factors such as Hepatocyte Growth Factor ("HGF"), epidermal growth factor ("EGF"), Interleukin-11 ("IL-11"), glucagon-like peptide ("GLP-2"), and insulin-like growth factors such as insulin-like growth factor-1 (IGF-1) may also be included with the administration of leptin or provided separately.

Leptin may be useful for treating patients suffering from inadequate intestinal function. As used herein, "inadequate intestinal function" means absorption levels of amino acids and sugars below that for a normal intestine. Conditions that may be treated with leptin include, but are not limited to, short bowel syndrome and processes producing inflammation of the bowel which includes, but is not limited to, necrotizing enterocolitis, intestinal atresia, midgut volvulus, severe acute gastroenteritis, chronic gastroenteritis, cholera, inflammatory bowel disease ("IBD") such as, Chronic Ulcerative Colitis ("CUC") and Crohn's Disease ("CD"), and other chronic infections of the bowel, and any condition that will benefit from an increase in intestinal function.

It will be appreciated that the present invention will also have application for treating intestinal disorders in subjects having immunologic disorders and immunodeficiency syndromes such as HIV and the like.

The following Examples are merely to provide exemplification of preferred embodiments of the invention, and should not be construed as providing any limitation on the scope of the invention which is described in the specification and the appended claims.

EXAMPLE 1

Twenty young adult male Sprague-Dawley rats weighing 200–225 g were used in this study. All rats had placement of lugutar venous catheters using PE-60 polyethylene tubing (Clay Adams, Parsippany, N.J.) connected to a subcutaneously placed osmotic minipump (model 2002. Alza Corp, Palo Alto, Calif.) designed to deliver their contents at a constant rate for 14 days. Recombinant mouse leptin (OB) was used for these studies (R&D Systems, Minneapolis, Minn.) and reconstituted in 0.1% bovine serum albumin (0.1% BSA). The rats were divided into four groups based on the contents in the osmotic minipump: Group 1 (control, n=5), 0.1% BSA; Group 2 (n=5), OB 2×=6.25 µg/kg/day; Group 3 (n=5), OB 4×=18.25 µg/kg/day; Group 4 (n=5), OB 8×=43.75 µg/kg/day.

Absorption Studies—Following the 14-day infusion period, [$C^{14}$] galactose and glycine absorption was determined. Intestinal segments (measuring 10 cm) immediately proximal and distal to the measured mid point of the small intestine were perfused with the different substrates using an in vivo closed recirculation technique. To avoid the possible error of differential absorption in the two bowel segments, the substrate being measured was alternated between the proximal and distal segments in different animals. Twelve-gauge polyethylene catheters were placed in the proximal and distal ends of each intestinal segment and secured to form a water-tight seal. The catheters were attached to a small roller pump to create a closed-recirculation system. The intestine was continuously perfused at 3 ml/h for 4 hours. The perfusate consisted of either [$C^{14}$] galactose (1 $\mu$Ci/10 ml) or [$C^{14}$] glycine (1 $\mu$Ci/10 ml) added to their respective unlabeled 5 mmol/L stock solutions prepared in phosphate-buffered saline. The perfusate also contained [$H^3$]-inulin (5 $\mu$Ci/10ml), which served as a nonabsorbable marker to control for loss of substrate from mechanisms other than absorption. Absorption was determined by the appearance from the reservoir of the labeled substrate compared with the labeled nonabsorbable marker. Substrate absorption, expressed as micromoles of substrate absorbed per square centimeter of intestinal segment, is calculated according to the following formula $(1-dpm_f/dpm_i)(InR)$ (Ci) $(V_e)/cm^2$ intestine where $dpm_f$ equals the final disintegrations per minute, $dpm_i$ equals the initial disintegrations per minute of test substance, InR equals the $dpm_f/dpm_i$ for insulin, Ci equals the concentration of test material in micromoles per milliliter, and $V_e$ equals the circulated volume in millimeters corrected for sampling.

DNA and RNA extraction—After completion of the absorption studies, biopsy specimens of the small intestine mucosa were obtained for determination of mucosal DNA and RNA content. Mucosal DNA content was determined using a standard diphenylamine procedure. Total RNA was extracted by homogenizing 30 mg small bowel mucosa in 4M guanidine thiocynate. The lysate was applied to a Qiagen RNeasy column (Qiagen, Chatsworth, Calif.), and total RNA recovered according to the manufacturer's instructions. RNA was quantified by $A_{260}$ and the quality was assessed by the $A_{260}/A_{280}$.

RT/PCR Analysis—Total RNA (1 $\mu$g) was brought up to 10 $\mu$l in DEPC-treated water. The sample was heated to 75° C. for 3 min, placed on ice, and cDNA synthesis was performed by reverse transcription for 15 min at 42° C. in a 20 $\mu$l reaction containing 1×PCR buffer 11 (Perkin-Elmer). 5 mM $MgCl_2$, 1.25 mM each dNTP, U/$\mu$l RNasin (Promega), 12.5 $\mu$g/$\mu$l oligo (dt) 15, and 2.5 U/$\mu$l AMV reverse transcriptase (Promega). Subsequent amplification of the cDNA sequence is performed with 10 $\mu$l of the reverse transcription reaction in 1×Taq buffer, 5% DMSO, 25 pmol each primer (Table 1), and 1.25 U Taq polymerase in a 50 $\mu$l reaction volume. SGLT and GLUT-5 were multiplexed with GAPDH to assess the relative levels of these transcripts. The temperature profile for the PCR reactions consists of a 2 min melting step at 95° C., then 30 cycles of 30 s at 94° C., 30 s at 55° C., and 90 sec at 65° C., followed by a final extension step of 5 min at 65° C. RT-PCR products were separated by size on a 4% agarose gel and stained with ethidium bromide. Images were transferred to an Apple MacIntosh Quadra 800 via an Eagle Eye still video imagine system, and the relative band intensities were analyzed with NCSA Gelreader Version 2.07 software.

Statistical analysis—All analyses were performed using the comparison of means model (ANOVA). Post hoc (LCD) analyses were performed to determine differences between control and treated groups. Data are expressed as mean+ standard error of the mean and $p<0.05$ was used as a determinant of statistical significance.

TABLE I

| Primers | | | Band Size (bp) |
|---|---|---|---|
| GAPDH | Forward | GGT CGG TGT GAA CCG GAT T (SEQ. ID. NO. 1) | 350 |
| | Reverse | GAG ATG ATG ACC CTT TTG (SEQ. ID. NO. 2) | |
| SGLT | Forward | GGA CTT CGA GGC CTG ATG CTG TC (SEQ. ID. NO. 3) | 270 |
| | Reverse | GTA ACT GGT GAT GGA CTG GAT GT (SEQ. ID. NO. 4) | |
| GLUT-5 | Forward | GGT ACA ACG TGG CTG CTG TCA AC (SEQ. ID. NO. 5) | 320 |
| | Reverse | CCT GCA CAT ATT CCA ACC AGA AGT (SEQ. ID. NO. 6) | |

Sequences of primers used in the RT/PCR experimentals. Sequences read 5-prime to 3-prime, left to right. Primers sequences determined from published Genbank sequences.

Absorption studies—After 14 days of exposure to leptin, both sugar and amino acid absorption were significantly increased (Table 2.) Specifically, glycine absorption, a marker of amino acid absorption, was increased significantly 1.5-*, 2.5-, and 2-fold greater than the control at the stated leptin doses, respectively (significance *$p<0.05$ and $p<0.01$.) As for sugar absorption, determined using galactose, 2×, 4×, and 8×doses of leptin produced absorption levels of 2.3, 2.7**. and 2.19*, respectively, which are significantly higher than control 1.58 (significance *$p<0.05$ and **$p<0.01$.) these increases represent 1.46-. 1.72-. and 1.39-fold above control levels. In both experiments, the 4×dose produced the greatest increases in absorption of both sugar and amino acid.

Table 2 shows the absorption data for both sugar, represented by galactose, and amino acid, represented by glycine. Increases are above control values. Significance is compared to control.

TABLE II

| Leptin Dose | N | Mean | SD | Increase | Significance |
|---|---|---|---|---|---|
| a. Galactose Absorption | | | | | |
| Control | 5 | 1.57 | 0.18 | | |
| 2X | 5 | 2.3 | 0.34 | 1.46-fold | 0.006 |
| 4X | 5 | 2.7 | 0.14 | 1.72-fold | 0.000 |
| 8X | 5 | 2.19 | 0.62 | 1.39-fold | 0.017 |
| b. Glycine Absorption | | | | | |
| Control | 5 | 1.55 | 0.28 | | |
| 2X | 5 | 2.34 | 0.64 | 1.49-fold | 0.025 |
| 4X | 5 | 3.32 | 0.32 | 2.15-fold | 0.000 |
| 8X | 5 | 3.1 | 0.6 | 2-fold | 0.000 |

Figure 1:
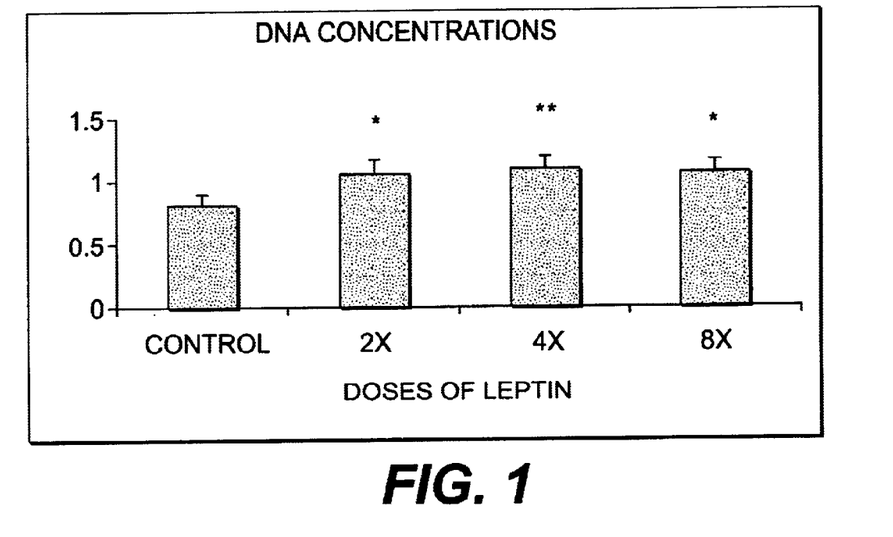
FIG. 1 is a plot showing DNA concentrations measured from the mucosa of the normal small intestine.

DNA Studies—DNA quantities were measured as a marker of mucosal mass of the rat small intestine, As shown in FIG. 1, DNA levels for the control group were 0.8 and 1.06, 1.1, and 1.07 for leptin doses of 2×, 4×, and 8×. This correspondence increases of 1.33-*, 1.38-**, and 1.34-fold*, respectively (significance *$p<0.05$ and **$p<0.01$).

Figure 2:
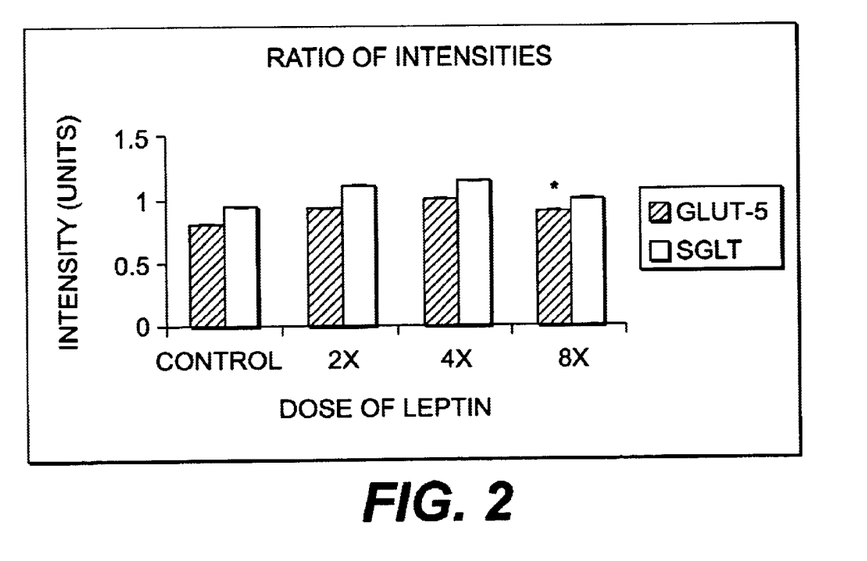
FIG. 2 is a plot showing the ratio of intensities for either SGLT or GLUT-5 to GAPDH.

RT/PCR Studies—Ratios of intensities of GAPDH and SGLT or GLUT-5 transcripts were compared between leptin-treated groups and the control. The results are shown in FIG. 2.

GLUT-5 is involved in the active transport of sugar into the mucosa of the small intestine. Doses of leptin 2×, 4×, and 8×increased GLUT-5 expression 1.17-, 1.26-, and 1.16-fold above control 0.8 to 0.94*, 1.01**, and 0.924*, respectively (significance *p<0.05 and **p<0.01). The same doses of leptin increased the expresson of SGLT, involved in amino acid transport into the mucosa of the small intestine. In this study, levels of expression were increased to 1.11, 1,14, and 1.01 from 0.945 control levels by lepth doses of 2×, 4×, and 8×, respectively. These increases translate to 1.17-, 1.21-, and 1.07-fold, respectively. Once again, the greatest increase for the expression of proteins involved in absorption was produced by the 4×dose of leptin.

Recent studies have described diverse effects of leptin. Centrally, leptin plays and important rale In energy regulation. Peripherally leptin is involved in hematopoesis, organ maturation, and development.

Without intending to be bound by theory, a possible mechanism for leptin's action is by increasing mucosal mass as indicated by the DNA results. Leptin increased DNA concentrations significantly at all the doses tested.

Leptin also increased the expression of markers involved in transport of sugars and amino adds GLUT-5 and SGLT. These results show that leptin has a potent effect on improving above normal levels the function of the small intestine in vivo.

EXAMPLE 2

Twenty-one adult male Sprague-Dawley rats weighing between 200 and 225 g were used for this study. After general anesthesia with ketamine and xylazine, all rats underwent an approximate 80% small bowel resection leaving 5cm of jejunum from the ligament of Trietz and 5cm of ileum from the ileocecal valve. After an end-to-end jejunoileal anastomosis was performed, the abdomen was closed and the rats were returned to their cages. Seven days after the massive small bowel resection, a systemic infusion was accomplished using a jugular venous catheter connected to a subcutaneously placed osmotic minipumps (model 2002, Alza Corp, Palo Alto, Calif.). These pumps are designed to deliver their contents of the osmotic minipump: group 1, 0.1% bovine serum albumin (control, n=7); group 2, leptin 2 $\mu$g/kg/d (n=7); group 3, leptin 4 $\mu$g/kg/d (n=7). The doses of leptin were derived from the dose-response curves of previous studies using normal rat intestine.

After the 14 day systemic infusion [$C^{14}$] galactose absorption was measured in the remaining small intestine of each rat using an in-vivo closed, recirculation technique. Galactose is a six-carbon sugar that is absorbed by passive and active transport. It has been used as a measure of carbohydrate absorption. Twelve-gauge polyethylene catheters were place in the remaining small intestine and secured to form a water-tight seal. The catheters were attached to a small roller pump to create the closed recirculation system. The intestine was continuously perfused at 15 mL/h for 4 hours. The perfusate consisted of [$C^{14}$] galactose (0.1 $\mu$Ci/mL) added to a 5 mmol/L stock solution of unlabeled galactose prepared in phosphate-buffered saline. The perfusate also contained [$H^3$] insulin (0.5 $\mu$Ci/mL), which served as a nonabsorbable marker to control for loss of substrate from mechanisms other than absorption. Absorption was determined by the disappearance from the reservoir of the labeled substrate in comparison wit the labeled nonabsorable marker. Substrate absorption, expressed as micromoles of substrate absorbed per square centimeter of intestinal segment, is calculated according to the following formula: $(1-dpm_f/dpm_i)$ (InR) $(C_i)$ $(V_e)/cm^2$ intestine where $dpm_f$=the final disintegrations per minute, $dpm_i$=the final disintegrations per minute, $dpm_i$= the initial disintegrations per minute of test substance, InR=$dpm_f/dpm_i$ for inulin, $C_i$=the concentration of test material in micromoles per milliliter, and $V_e$=the circulated volume in milliliters.

After completion of the absorption study, the perfused intestinal segment is opened along its mesenteric border and the length and width measured to determine the surface area. While this is not a true surface area because it does not measure the surface area of the villi, this measurement is more accurate than expressing absorption per unit length (cm) as is more commonly done. The mucosa is then collected and frozen for future analysis. Mucosal DNA content was determined using the Wizard Genomic DNA Purification Kit (Promega, Madison, Wis.). Mucosal RNA was extracted and RT-PCR was performed using the following primers: sodium/glucose co-transporter (SGLT-1), fructose transporter (GLUT-5), and glyceraldeyde-3-phosphate dehydrogenase (GAPDH) which was used as the internal standard. PCR products were separated on a 4% agarose gel and relative band intensities were measured.

The data are expressed as the mean±SEM and statistical significance was determined using analysis of variance.

The results for intestinal absorption, mucosal DNA content, and relative band intensities of RT-PCR products are shown in Table III.

TABLE III

Absorption, DNA content, and band intensities after 2 weeks of systemic leptin administration.

| Groups | Galactose Absorption ($\mu$moles/cm$^2$) | DNA Content ($\mu$g/mg mucosa) | SGLT (band intensity) | GLUT-5 (band intensity) |
|---|---|---|---|---|
| 1 | 1.63 + 0.6 | 8.81 + 1.2 | 1.08 + 0.3 | 0.84 + 0.2 |
| 2 | 2.36 + 0.11* | 9.01 + 0.49 | 1.09 + 0.8 | 0.96 + 0.4* |
| 3 | 1.80 + 0.42 | 9.59 + 0.41 | 1.13 + 0.2 | 0.92 + 0.04 |
|   | (*p < 0.01) |   |   | (*p < 0.05) |

Figure 3:
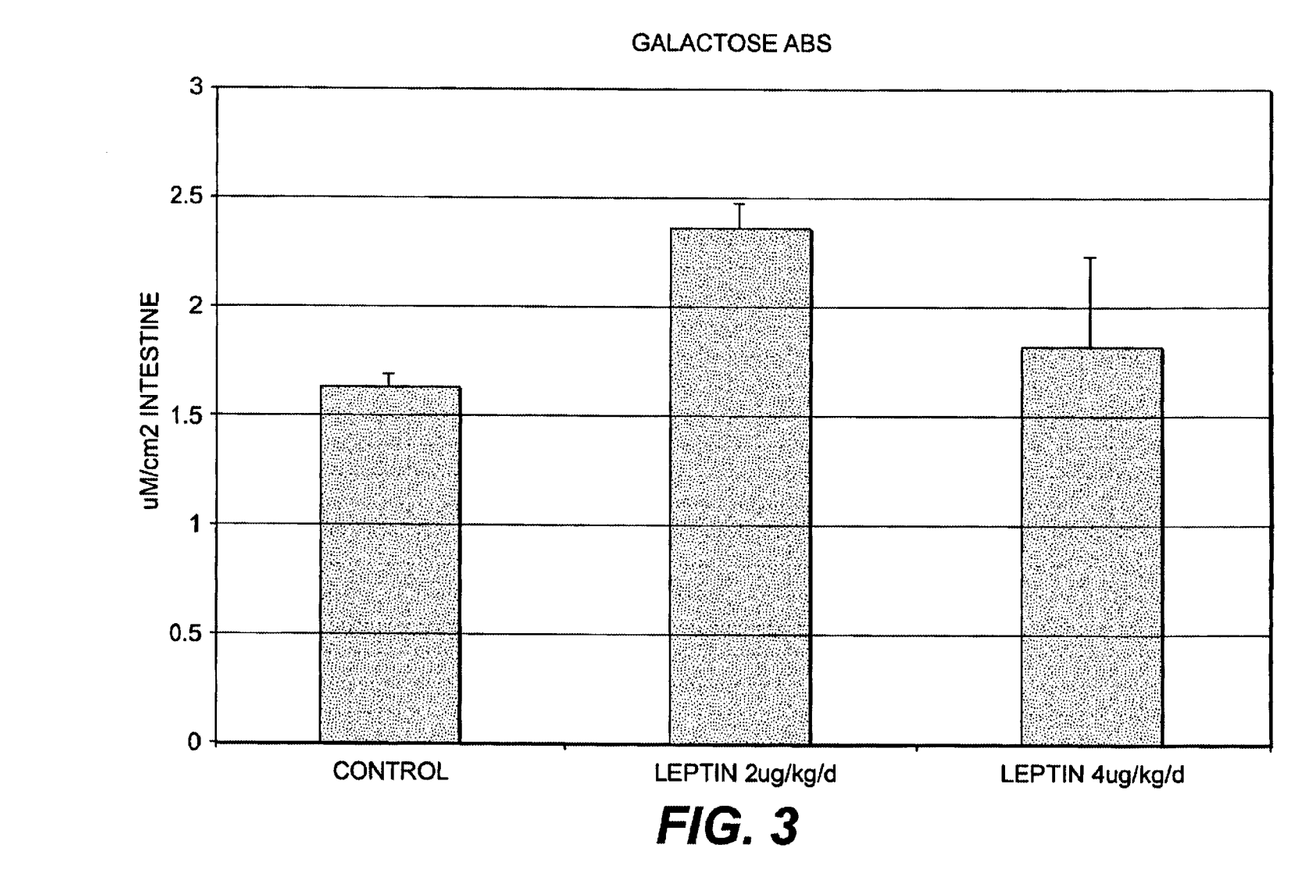
FIG. 3 is plot showing galactose absorption per surface area of intestine ($cm^2$).
Figure 4:
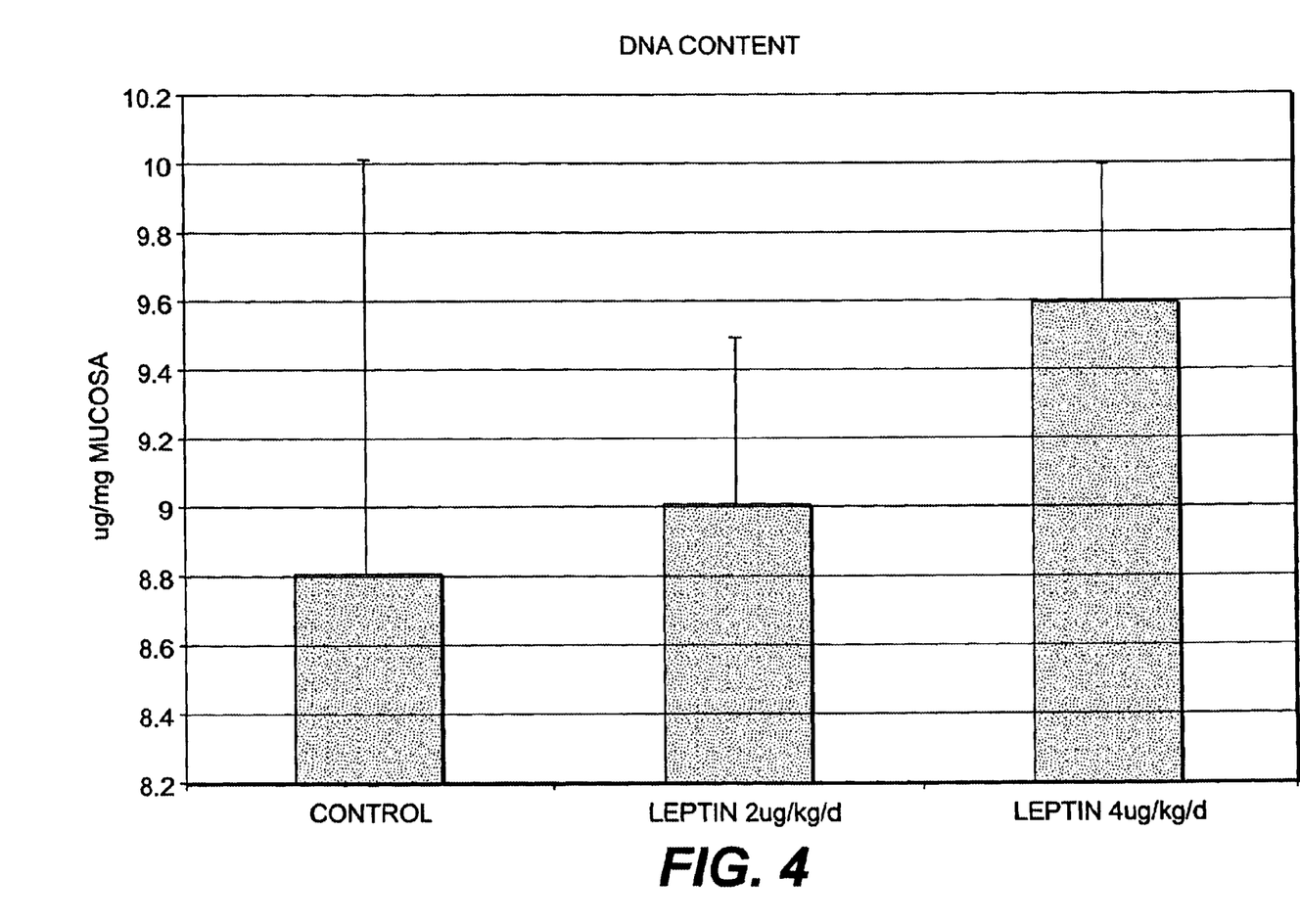
FIG. 4 is a plot showing the DNA content per microgram of mucosa.
Figure 5:
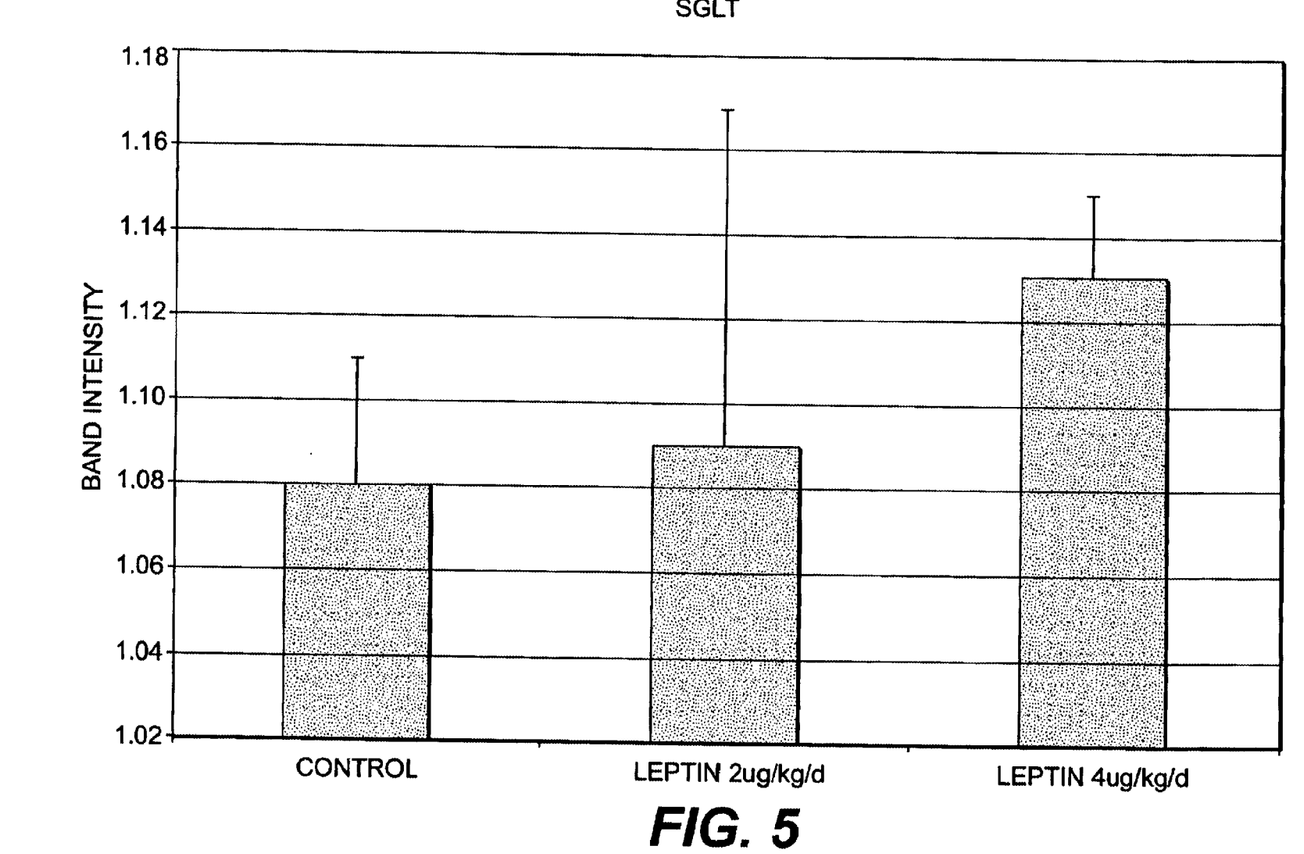
FIG. 5 is a plot showing the SGLT band intensity relative to GAPDH (internal standard).
Figure 6:
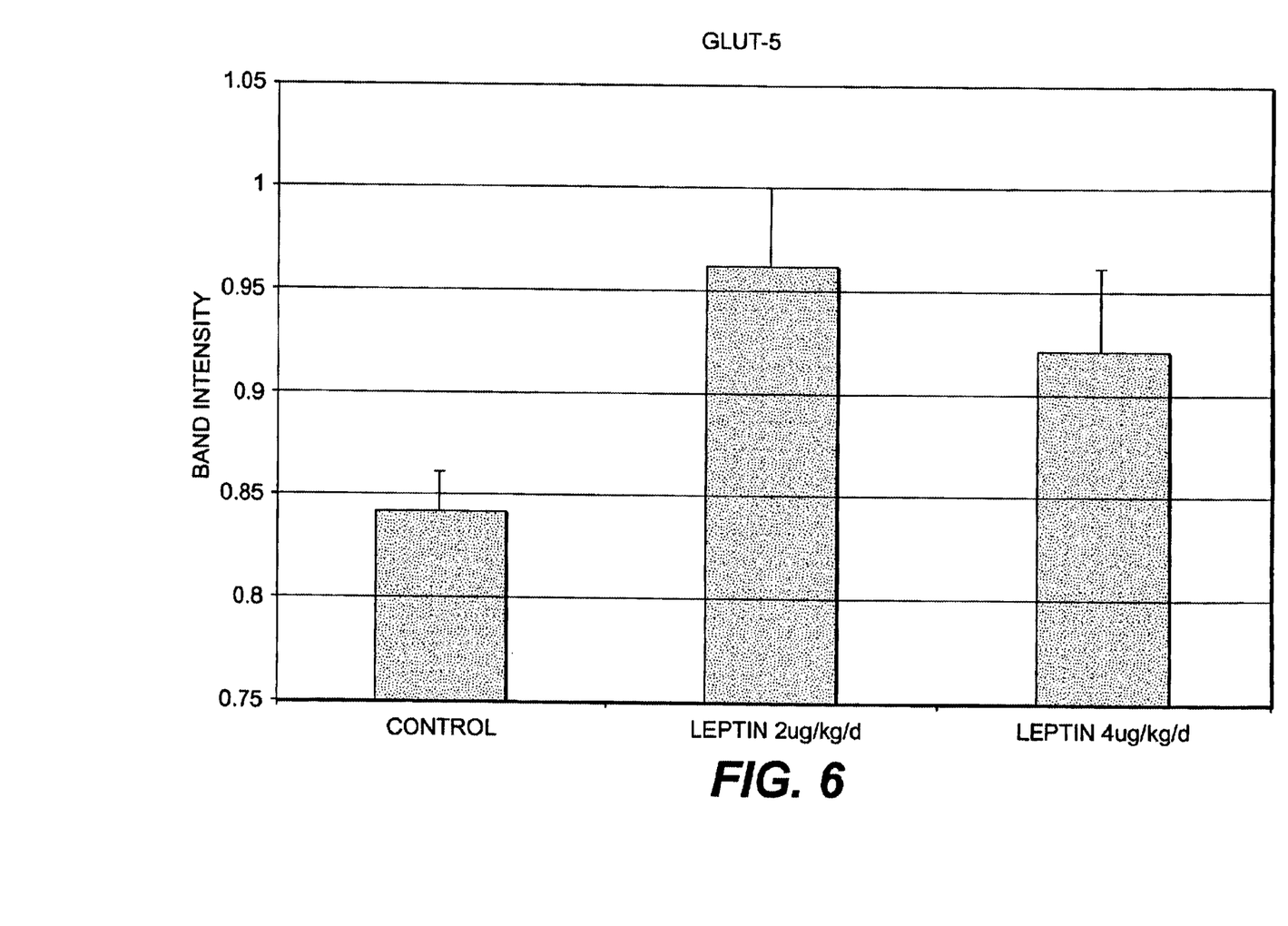
FIG. 6 is a plot showing the GLUT-5 band intensity relative to GAPDH.

Galactose absorption per surface area of intestine (cm$^2$) was increased significantly (44%; P<0.01) in Group 2 (leptin 2 $\mu$g/kg/d), but not in Group 3 (leptin 4 $\mu$g/kg/d) when compared to Group 1 (control) (FIG. 3). DNA content per microgram of mucosa appeared to be increased in Group 3, however the results were not statistically significant (FIG. 4). SGLT band intensity relative to GAPDH (internal standard) also appeared to be increased in Group 3, however these results were not statistically significant (FIG. 5). GLUT-5 band intensity relative to GAPDH was increased significantly in Group 2 (14% increase, P<0.05) (FIG. 6).

After massive small bowel resection, the remaining intestine undergoes an adaptive response which increases the absorptive capacity of the mucosa per unit area. When the adaptive response is insufficient to meet the nutritional needs of the patient, short bowel syndrome is the result. This is particularly devastating to children, who have increased caloric requirements in order to support normal growth and development.

Our results suggest that systemic infusion of a moderate dose of leptin enhances the ability of small intestine mucosa to absorb carbohydrate beyond the normal adaptive response. Group 2, which produced the most significant increase in absorption, received a daily dose of leptin which was eight times the physiologic concentration (3.1 ng/ml) in rat serum. Group 3 received sixteen times the physiologic concentration per day. Interestingly, the lower doses of leptin had a larger effect on mucosal absorption.

Without intending to be bound by theory, a mechanism for this increase in absorptive capacity is suggested by the increased gene expression of the GLUT-5 glucose transporter. With the knowledge that leptin receptors are abundant in the small intestine these results indicate a possible local effect of leptin on sugar transport in intestine mucosal cells.

These results demonstrate that leptin can increase mucosal absorptive capacity and increase glucose transport gene expression in a rat model of short bowel syndrome.

It will be readily understood by those persons skilled in the art that the present invention is susceptible to broad utility and application. Many embodiments and adaptations of the present invention other than those herein described, as well as many variations, modifications and equivalent arrangement, will be apparent from or reasonably suggested by the present invention and the foregoing description without departing from the substance or scope of the present invention.

Accordingly, while the present invention has been described in detail in relation to its preferred embodiment, it is to be understood that this disclosure is only illustrative and exemplary of the present invention and is made merely for purposes of providing a full and enabling disclosure of the invention. The foregoing disclosure is not intended to be construed to limit the present invention or otherwise exclude any other embodiments, adaptations, variations, modifications or equivalent arrangements, the present invention being limited only by the claims and the equivalents thereof.

What is claimed is:

1. A method for increasing intestinal function comprising administering leptin in an amount effective to increase intestinal absorption of amino acids and sugars in a patient having inadequate amino acid and sugar absorption that results in malnutrition.

2. The method of claim 1 wherein the step of administering leptin to a patient comprises administering leptin in an amount effective to increase mucosal mass in the intestine of the patient.

3. The method of claim 1 wherein leptin is administered in an amount ranging from about 1 μg/kg body weight/day to about 50 μg/kg body weight/day.

4. The method of claim 1 wherein leptin is administered in an amount ranging from about 2 μg/kg body weight/day to about 20 μg/kg body weight/day.

5. The method of claim 1 wherein said patient has a condition selected from the group consisting of short bowel syndrome, inflammation of the bowel, chronic ulcerative colitis, Crohn's Disease, necrotizing enterocolitis, intestinal atresia, midgut volvulus, severe acute gastroenteritis, chronic gastroenteritis, cholera, chronic infections of the bowel, and immunologic disorders affecting the small intestine.

6. A method for increasing intestinal function comprising administering leptin in an amount effective to increase intestinal mucosal mass in a patient having inadequate intestinal mucosal mass that results in malnutrition.

7. The method of claim 6 wherein leptin is administered in an amount ranging from about 1 μg/kg body weight/day to about 50 μg/kg body weight/day.

8. The method of claim 6 wherein leptin is administered in an amount ranging from about 2 μg/kg body weight/day to about 20 μg/kg body weight/day.

9. The method of claim 6 wherein said patient has a condition selected from the group consisting of short bowel syndrome, inflammation of the bowel, chronic ulcerative colitis, Crohn's Disease, necrotizing enterocolitis, intestinal atresia, midgut volvulus, severe acute gastroenteritis, chronic gastroenteritis, cholera, chronic infections of the bowel, and immunologic disorders affecting the small intestine.

* * * * *